US006337071B1

United States Patent
Molyneux

(10) Patent No.: US 6,337,071 B1
(45) Date of Patent: Jan. 8, 2002

(54) MOSQUITO AND/OR FLEA CONTROL

(76) Inventor: William Mitchell Molyneux, PO Box 201, Montrose Victoria 3765 (AU)

(*) Notice: Subject to any disclaimer, the term of this patent is extended or adjusted under 35 U.S.C. 154(b) by 0 days.

(21) Appl. No.: 08/878,835

(22) Filed: Jun. 20, 1997

(30) Foreign Application Priority Data

Jun. 21, 1996 (AU) .............................................. PO0605

(51) Int. Cl.⁷ .............................................. A62K 35/78
(52) U.S. Cl. ...................... 424/195.1; 424/405; 514/703
(58) Field of Search .............................. 424/195.1, 405; 514/703

(56) References Cited

U.S. PATENT DOCUMENTS

| 4,049,828 A | * | 9/1977 | Cole ........................... 514/703 |
| 4,946,682 A | * | 8/1990 | Stirnadel et al. ......... 424/195.1 |
| 5,298,250 A | * | 3/1994 | Lett et al. .................... 424/405 |
| 5,346,922 A | * | 9/1994 | Beldock et al. ............. 514/703 |

FOREIGN PATENT DOCUMENTS

EP   0 695 509   2/1996

OTHER PUBLICATIONS

Merck Index, tenth edition, p. 2301, 1983.*

* cited by examiner

Primary Examiner—James H. Reamer
(74) Attorney, Agent, or Firm—D. Peter Hochberg

(57) ABSTRACT

A plant of the species *Leptospermum liversidgei* which is able to block the carbon dioxide message to mosquitoes and/or fleas within the vicinity of its locus.

Figure 1:

The present invention also provides a crude or refined essential oil extract from the said plant.

Another aspect of the invention provides a method for repelling mosquitoes and/or fleas comprising the cultivation of the said plant.

A further aspect of the invention provides another method for repelling mosquitoes and/or fleas comprising the use of the said essential oil extract from the said plant.

12 Claims, 4 Drawing Sheets (4 of 4 Drawing Sheet(s) Filed in Color)

MOSQUITO AND/OR FLEA CONTROL

FIELD OF THE INVENTION

This invention is in the field of mosquito and/or flea control.

In one aspect the invention relates to a plant which has mosquito and/or flea repellent properties.

In another aspect the invention provides an oil extract from the said plant which, in various forms and by various means, may be used as a mosquito and/or flea repellent.

BACKGROUND TO THE INVENTION

A mosquito's and/or flea attraction to warm blooded animals is partly by body warmth and also by carbon dioxide as expelled breath. Certain vaporous substances, such as essential oils, are able to block the carbon dioxide message thus falsely indicating to the mosquito and/or flea that the animal is simply a source of warmth like a light globe or candle.

Many species of plants, such as tea-tree (Leptospermum SP), are known to produce a large amount of complex mixtures of oils which are stored in their tissues.

It is an object of this invention to isolate and characterise a true breeding clone of a plant which, by virtue of its oil content, is able to act as a mosquito repellent.

Such mosquito and/or flea repellency can occur by oxidisation of the oils from the leaves and stems of the plant directly into the surrounding atmosphere. Alternatively the oils may be extracted from the plant tissue and this extract may be used in aerosol sprays or dispersants or in pharmaceutical preparations suitable for direct topical application to the skin of a human or other warm blooded animal.

SUMMARY OF THE INVENTION

The present invention provides:

a plant of the Genus Leptospermum species liversidgei which is able to block the carbon dioxide message to mosquitoes and/or fleas within the vicinity of its locus.

The present invention also provides a crude or refined essential oil extract from the said plant.

Another aspect of the invention provides a method for repelling mosquitoes and/or fleas comprising the cultivation of the said plant.

A further aspect of the invention provides another method for repelling mosquitoes and/or fleas comprising the use of the said essential oil extract from the said plant.

PREFERRED ASPECTS OF THE INVENTION

It is advantageous if the plant according to the invention, is aesthetically attractive and thus is suitable as an ornamental plant. The most preferred morphological characteristics are those given in FIGS. 1 and 2.

The oil which is most suitable for the purpose of the invention is citronellal however the citronellal analogues isopulegol and pulegol are also effective.

A plant according to the invention will have a citronellal and/or analogue content which falls substantially within the range of at least 55–95% of total extractable volatile oil content. (Throughout this specification, the proportions of oil content are expressed as area percentages measured as areas under peaks by gas-chromatography.)

The oil content may exhibit seasonal and/or regional variation but it is preferred that it will be at least 70% citronellal and/or analogues.

This content may be made up of amounts of citronellal, isopulegol and pulegol which fall substantially within the ranges of 59–68%, 9–14% and 0–5% respectively.

The most preferred clone of the plant which exhibits the desired morphological features and oil content is genetically characterised by the Randomly Amplified Polymorphic DNA (RAPD) fragment analysis given in FIG. 3.

An essential oil mixture may be extracted from the tissues of the plant according to the invention.

It is preferred that the extracted oil will contain 55–95% citronellal and/or the citronellal analogues isopulegol and pulegol. It is more preferred that the oil will comprise at lease 70% citronellal and/or analogues.

The most preferred embodiment of this aspect of the invention is an essential oil extract from the plant identified by the RAPD fragment analysis given in FIG. 3.

The plant according to the invention may be used as a mosquito repellent by planting one or more shrubs in either outdoor or indoor situations. Mosquito and/or flea repellency preferably occurs by oxidisation into the surrounding air of oils from the leaves and stems of the plants. Alternatively the leaves may be manually crushed or bruised to promote the efflux of the oils.

An extracted oil from the plant according to the invention may be used in a method for repelling mosquitoes and/or fleas. The oil may be vaporised by any means known in the art such as a thermal vaporiser (for example an oil burner or other heating device) or by impregnation into a vapour dispersion block or gel.

Alternatively, the oil may be applied directly to the skin or clothing of a human or animal. In this case it is preferred that the oil is mixed with appropriate pharmaceutical carriers or excipients which make it suitable for topical application. Examples of such preparations include soaps, alcohol based creams or lotions, oil-based creams and zinc-based creams.

These methods for repelling mosquitoes may be used individually or in combination with each other.

DESCRIPTION OF THE FIGURES AND TABLES

The file of this patent contains at least one drawing executed in color.

Figure 2:
Figure 3A:
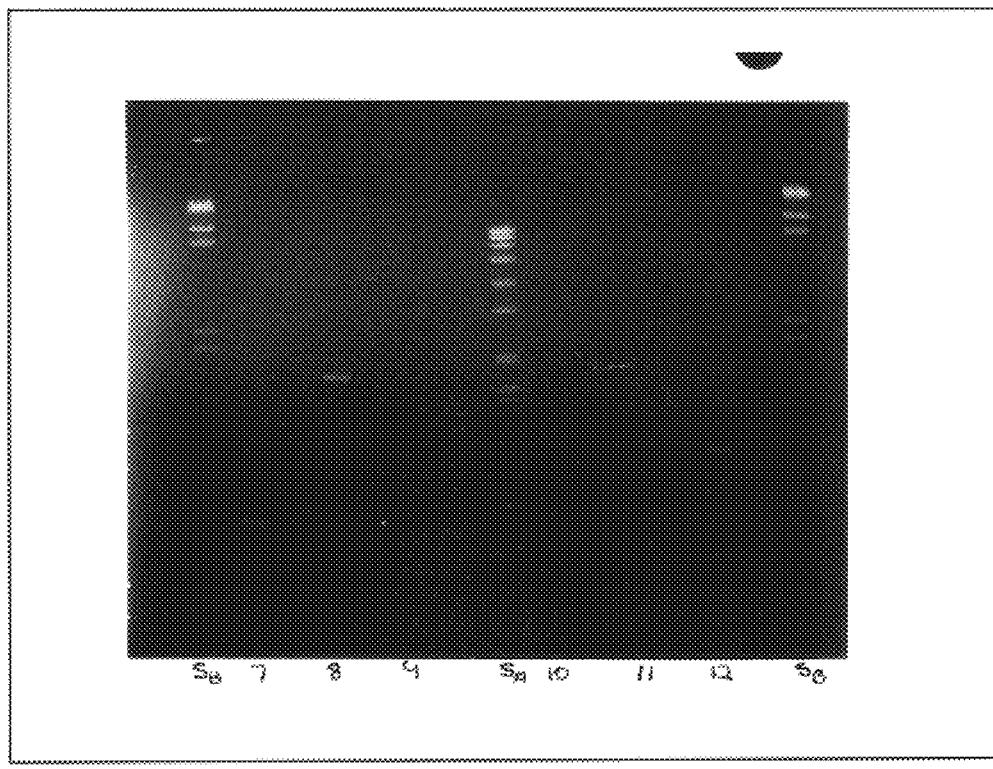
Figure 3B:
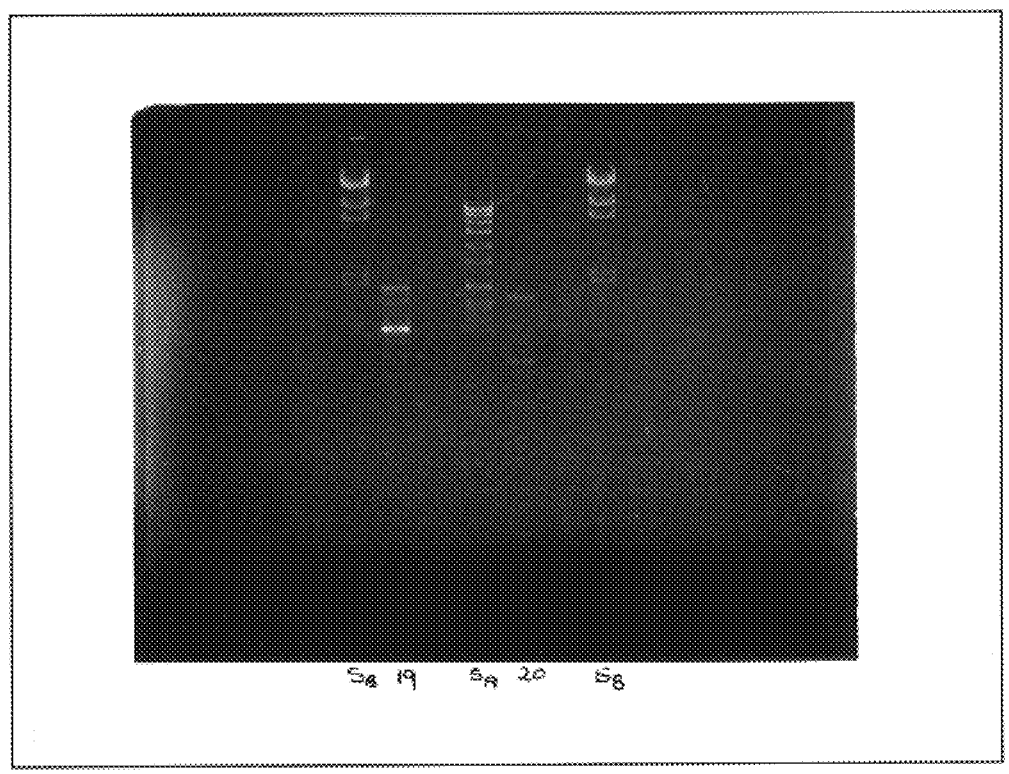
Figure 3C:
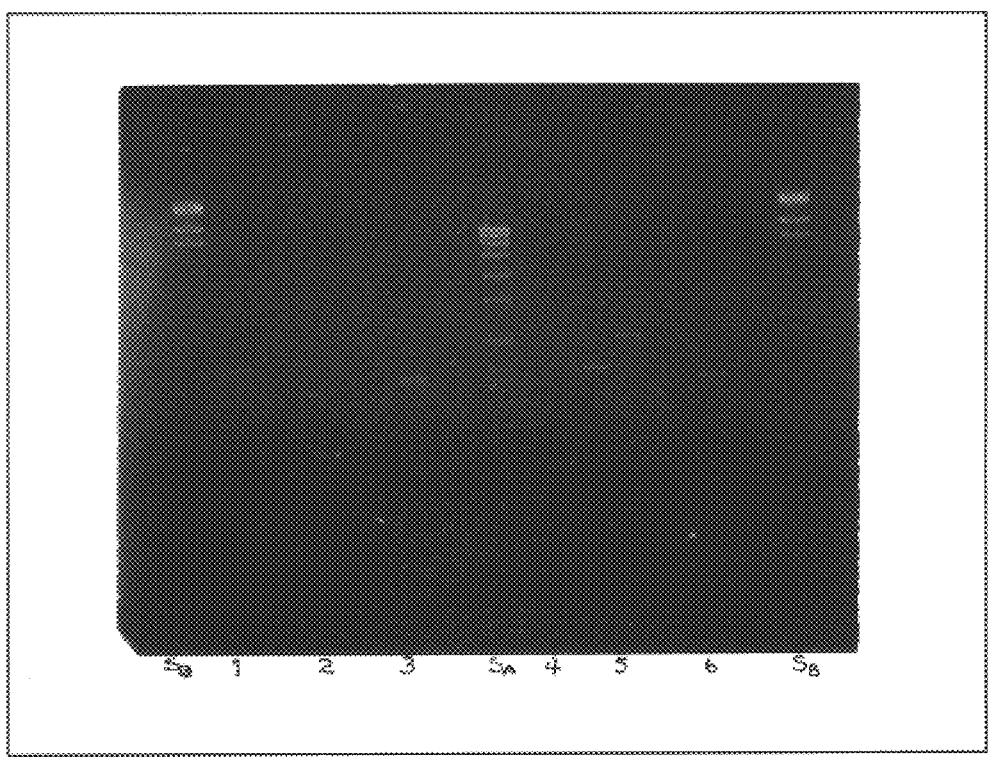
Figure 3D:
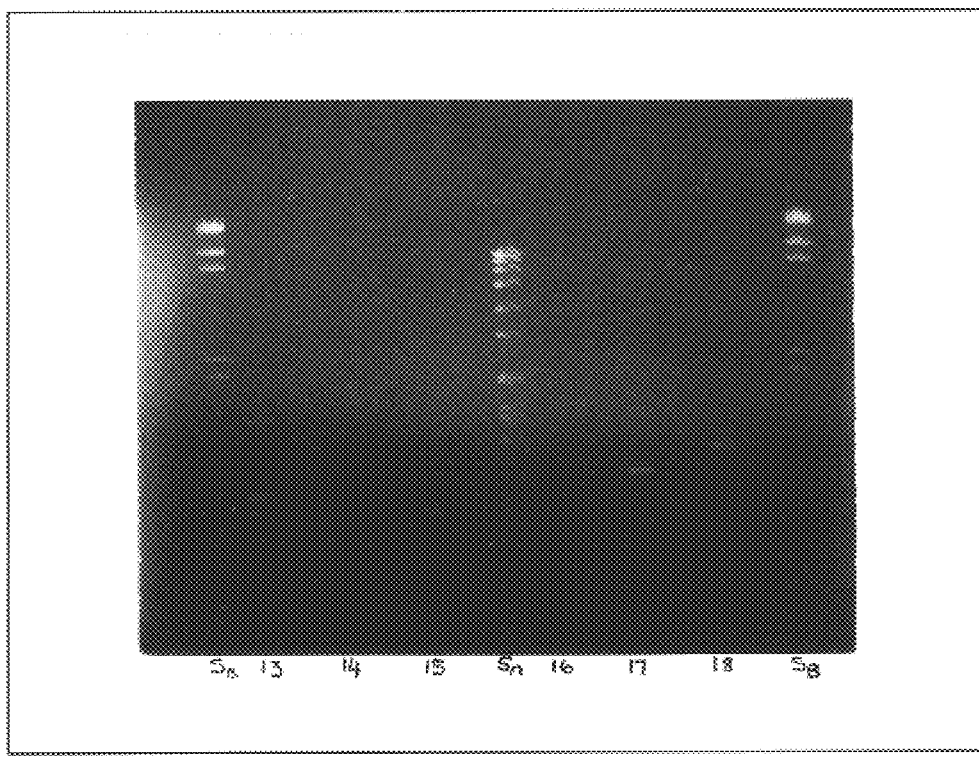

FIG. 1 is a illustration of the most preferred clone of *Leptospermum liversidgei* according to the invention, FIG. 2 is a sketch of the same plant depicted in FIG. 1 with colours of the various parts identified by RHS Colour Coding Standards, FIGS. 3A–D shows the results of Randomly Amplified Polymorphic DNA (RAPD) fragment analysis of the plant shown in FIG. 1, Table 1 characterises the DNA restriction fragments which were used as standards of known size for comparison with the RAPD fragments in FIG. 3, Table 2 shows the results of gas chromatographic analysis of ethanolic extracts of leaf tissue from various individual plants according to the invention, Table 3 gives details of the analysis parameters for the gas chromatographic mass spectrometric analysis of essential oil extracts, Table 4 shows the results of gas chromatographic mass spectrometric analysis of oils extracted from the most preferred clone of the plant according to the invention, Table 5 shows the nucleotide sequences of the primers used to generate RAPD fragments, and Table 6 sets out the cycling conditions used in the PCR amplification of DNA for RAPD analysis.

DETAILED DESCRIPTION WITH RESPECT TO THE FIGURES AND TABLES

Morphology

Leptospermum liversidgeiBaker & Smith

See FIGS. 1 and 2. Shrub, erect, compact, 0.5–2.5 (3) meters tall and 1–1.5 meters wide, mostly single trunked; branches numerous, erect, ends occasionally lightly weeping, sericeous, soon becoming glabrous.

Bark hard, tight, grey, flaking in patches near base.

Leaves shortly petiolate, alternate, densely arranged up the stems, seldom spreading, flexible, apex obtuse, 3–8 mm long×1.5–3.5 mm wide, glabrous, new growth RHS Green group 141C; mature leaves RHS Green group 141A, oil glands small, numerous, emitting a citrus-like scent when crushed.

Flowers solitary, ±sessile, mainly in axils; hypanthium 3–5 mm long×3–4 mm wide, glabrous or occasionally sparsely sericeous; sepals ca 1.5 mm long; petals light pink RHS Red group 56D, ca 5–7mm long×4–5 mm wide; stamens numerous C.15–20; ovary five locular, domed, glabrous.

Propagation of plant

Following clonal selection on the basis of tissue oil content, the plant has been propagated asexually through three generations using standard nursery techniques.

These include material cleansing, hormone stimulation, and root generation on heat beds in a glasshouse situation in a medium comprised of equal parts of peat and grade 500 perlite.

Growing-on has been carried out in a soil-less potting medium, comprising milled pinebark and coarse sand, with added trace elements and NPK fertiliser regime supplied by controlled release pellets.

Extraction and Analysis of Essential Oil Content

Leaf tissue was obtained in June from various individuals of *Leptospermum liversidgei*. Ethanolic extracts of each sample were analysed by the single leaf extract method published by Brophy at al, the disclosure of which is incorporated heroin by reference. (J J Brophy, N W Davies, I A Southwell, I A Skiff and L R Williams, Journal of Agricultural and Food Chemistry 1989, 37 1330–1335). Analysis was by a 60 mm×0.2 mmid AT35 FSOT gas chromatography column using hydrogen as a carrier gas.

Results of this analysis are shown in Table 2. The sample with the highest total citronellal and analogue level was No. BY11 with a figure of 73%.

A further sample of this most preferred individual was taken from cultivated material when the plant was vigorously growing in March. The following procedure was used to distill the essential oils from this material.

Leaf tissue was placed in a steam distillation vessel with some boiling chips. The vessel was then filled with water to cover the plant material. The distillation cover was securely attached with a wire clamp. A Dean and Stark apparatus and water cooled condenser were then attached using a stand and clamps for support. A hot plate was placed under the distillation vessel and adjusted to bring the contents to the boil.

The essential oil was removed from the plant material by the steam, which travelled upwards to the condenser where it cooled into liquid form, collecting in the Dean and Stark apparatus. The oil was the lower layer in the apparatus and was removed via the tap. The oil was then dried for analysis.

Analysis of the oil content was by gas chromatography and mass-spectrometry, by the parameters outlined in Table 3. As shown In Table 4, this analysis was able to identify pulegol as well as the isopulegol and citronellal identified earlier. The measurement of total citronellal/analogue content of the oil had increased by this method to 82.5%.

Genetic Characterisation of the Selected Clone

Genetic characterisation of BY11 was undertaken by generation of a Randomly Amplified Polymorphic DNA (RAPD) profile.

Firstly, DNA was isolated from leaf tissue of BY11 according to the method described by Fulton et al (T M Fulton, J Chunwongse and S D Tanksley, Plant Molecular Biology Reporter 1995 13, 207–209) the entire disclosure of which is incorporated herein by reference. The only modification to this method was the addition of 2% soluble polyvinyl pyrrolidone (PVP) to the micropreparation buffer.

RAPD fragments were then generated from aliquots of this DNA by the following protocol:

Twenty separate PCR DNA amplification reactions were carried out, each with a different primer (2-01 to 2-20, the sequences of which are shown in Table 5) under the cycling conditions set out in Table 6. The reaction mixtures contained: DNA, 50 ng; Primer, 0.4 $\mu$M; dNTPs, 100 $\mu$M; $Mg^{2+}$, 3 $\mu$M; X1 buffer; Amplitaq, 1.0 Unit, in a total reaction volume of 50 $\mu$l. When the reactions were complete, 20 $\mu$l aliquots of reaction product were sampled from each 50 $\mu$l reaction mixture and added to gel loading buffer. These samples were loaded onto a 1% agarose gel in X 1 TAE buffer and the gel was electrophoretically developed at 70V which separated the DNA fragments according to size. For comparison as known size standards, two separate preparations of Hind III and SPP1 restriction fragments of $\lambda$DNA (as shown in Table 1) were also loaded into the 1% agarose gel in an amount of 0.5 $\mu$g total DNA per lane. The resulting ethidium bromide stained fragments were visualised with UV light and recorded photographically as shown in FIG. 3.

TABLE 1

| SPP1 = Standard A ($S_A$) | | |
|---|---|---|
| Fragment No | Size (Kb) mean ± SD** | Molecular Weight* |
| 1 | 8.51 ± 0.07 | 5.62 × $10^6$ |
| 2 | 7.35 ± 0.06 | 4.85 × $10^6$ |
| 3 | 6.11 ± 0.06 | 4.03 × $10^6$ |
| 4 | 4.84 ± 0.03 | 3.19 × $10^6$ |
| 5 | 3.59 ± 0.01 | 2.37 × $10^6$ |
| 6 | 2.81 ± 0.01 | 1.85 × $10^6$ |
| 8 | 1.86 ± 0.02 | 1.23 × $10^6$ |
| 9 | 1.51 ± 0.01 | 0.99 × $10^6$ |
| 10 | 1.39 ± 0.02 | 0.92 × $10^6$ |
| 11 | 1.16 ± 0.01 | 0.76 × $10^6$ |
| 12 | 0.98 ± 0.01 | 0.64 × $10^6$ |
| 13 | 0.72 ± 0.00 | 0.47 × $10^6$ |
| 14 | 0.48 ± 0.01 | 0.32 × $10^6$ |
| 15 | 0.36 ± 0.01 | 0.24 × $10^6$ |

| $\lambda$ Hind III = Standard B ($S_B$) | | |
|---|---|---|
| Fragment No | No of Base Pairs | Molecular Weight |
| 1 | 23,130 | 15.26 × $10^6$ |
| 2 | 9,416 | 6.21 × $10^6$ |
| 3 | 6,557 | 4.32 × $10^6$ |
| 4 | 4,361 | 2.88 × $10^6$ |
| 5 | 2,322 | 1.53 × $10^6$ |
| 6 | 2,027 | 1.33 × $10^6$ |
| 7 | 564 | 0.37 × $10^6$ |
| 8 | 125 | 0.08 × $10^6$ |

TABLE 2

| Sample No. | apinene | linylool | citronellal | Iso-pulegol | un-identified (1) | un-identified (2) | B-oxy-ophyllene | un-identified (3) |
|---|---|---|---|---|---|---|---|---|
| BY11 | 0.6 | 1.5 | 59.2 | 13.3 | 4.0 | 8.6 | 1.4 | 4.5 |
| 13 | 8.1 | 2.6 | 48.0 | 12.0 | 2.5 | 6.1 | 2.9 | 4.8 |
| 16 | 1.2 | 1.2 | 50.5 | 10.9 | 2.9 | 11.2 | 1.4 | 3.4 |
| BY18 | 0.9 | 1.6 | 52.2 | 12.5 | 2.2 | 8.4 | 1.3 | 5.2 |
| 25 | 1.8 | 2.8 | 49.5 | 9.4 | 1.9 | 11.3 | 2.5 | 3.3 |

TABLE 3

| | |
|---|---|
| Instrument | Varian GC 3400/Saturn MS |
| Autosampler | Varian 8100 |
| Column | Dual J&W fused silica capillary, 0.25 micron DB5 coating |
| Column Size | 0.26 mm i.d. × 30 m |
| Sample size | 0.1 microliters of 4% solution in absolute alcohol |
| Split ratio | 20 to 1 |
| Carrier gas | Helium @ 60 psi, 1 ml/min |
| Make up gas | Nitrogen @ 40 psi |
| Injector temp | 250 deg C. |
| GC Detector | FID A |
| Detector temp | 250 deg C. |
| Oven temp initial | 60 deg C. |
| Oven temp final | 240 deg C. |
| Oven temp program rate | 3 deg/min from 60–240 deg C. |
| Final temp hold time | 2 min |
| FID Autozero | On |
| FID Attention | 8 |
| FID Range | 12 |
| Plot speed | 0.3 cm/min |
| Zero offset | 15% |
| Peak reject value | 30 |
| Signal to noise ratio | 6 |
| Tangent peak height | 5 |
| Initial peak width | 2 |
| Auxiliary temp | 240 deg C. |
| Manifold temp | 170 deg C. |
| Multiplier set voltage | 1700 volts |
| A/M amplitude set voltage | 3.5 volts |
| Low mass | 41 m/z |
| High mass | 320 m/z |
| Scan rate | 1000 millisecs |
| Segment acquire time | 62 min |
| Peak threshold | 1 count |
| Filament/multiplier delay | 2.00 min |
| Mass defect | 100 m$\mu$/100$\mu$ |
| Tune file | TUN_DFLT |
| Emission current | 20 microamps |
| AGC prescan ionisation time | 100 microsecs |
| AGC prescan storage level | 20.0 m/z |
| El backgrount mass | 45 m/z |
| RF dump value | 650.0 m/z |
| AGC target | 32500 counts |
| El max ionisation time | 25000 microsecs |

TABLE 4

BY11

| | |
|---|---|
| alpha Pinene | 0.7% |
| beta Pinene | 0.1 |
| Myrcene | 0.1 |
| Limonene + | |
| 1,8 Cincol | 0.1 |
| Linalool | 1.4 |
| iso Pulegol | 9.7 |
| Citronellal | 67.9 |
| Pulegol | 4.9 |
| nCO Menthol | 0.6 |
| Citonellol | 1.4 |

TABLE 4-continued

BY11

| | |
|---|---|
| Noral | 0.2 |
| Geraniol | 0.2 |
| Methyl citronellate | 0.1 |
| Geranial | 0.2 |
| Citronellyl acetate | 5.7 |
| t Methyl cinnamate + | |
| Geranyl acetate | 1.9 |
| beta Caryophyllene | 1.3 |
| alpha Humulene | 0.1 |
| Germacrene D | 0.1 |
| Germacrene B | 1.1 |
| Ledol | 0.1 |
| Spathulenol | 0.1 |
| Globulol | 0.5 |
| beta Eudesmol | 0.1 |
| | 95.6% identified |

TABLE 5

Sequence of primers

| Primers | Sequence 5'--------3' | Primers | Sequence 5'--------3' |
|---|---|---|---|
| 2-01 | AAGCTGCGAG | 2-11 | CCGAATTCCC |
| 2-02 | CACGGCGAGT | 2-12 | GGCTGCAGAA |
| 2-03 | CTGGCGTGAC | 2-13 | CTGACCAGCC |
| 2-04 | GGGTAACGCC | 2-14 | GTCCCGTGGT |
| 2-05 | CAATCGCCGT | 2-15 | CCACACTACC |
| 2-06 | TTCGAGCCAG | 2-16 | CACCCGGATG |
| 2-07 | GAACGGACTC | 2-17 | CACAGGCGGA |
| 2-08 | GTCCCGACGA | 2-18 | TGACCCGCCT |
| 2-09 | TGTCATCCCC | 2-19 | GGACGGCGTT |
| 2-10 | GGTGATCAGG | 2-20 | TGGCGCAGTG |

TABLE 6

| Cycle Number | Temperature (°C.) | Time | Step in Cycle |
|---|---|---|---|
| 1 | 94 | 1 min | denaturation |
| | 40 | 30 sec | annealing |
| | 72 | 1 min | extension |
| 2–34 | 94 | 10 sec | denaturation |
| | 40 | 30 sec | annealing |
| | 72 | 1 min | extension |

TABLE 6-continued

| Cycle Number | Temperature (°C.) | Time | Step in Cycle |
|---|---|---|---|
| 35 | 94 | 10 sec | denaturation |
| | 40 | 30 sec | annealing |
| | 72 | 5 min | extension |
| | 4 | Hold | |

The claims, illustrations and drawings, if any, form part of the disclosure of this specification as does the description, claims, illustrations and drawings of any associated provisional or parent specification or of any priority document, if any, all of which are imported hereinto as part of the record hereof.

Finally it is to be understood that various alterations, modifications and/or additions may be incorporated into the various constructions and arrangements or parts without departing from the spirit and ambit of the invention.

In this application, color determinations were established were established by reference to the Second Edition of the Royal Horticultural Society (RHS) Colour Chart. It is recommended that, because there are some differences in "standard" colors from one edition of the Chart to another (especially in the purplish red to purple to blue range), the Colour Charts should not be interchanged.

In addition, it should be noted that variations in perception of color can occur when viewed by different lights, and it has also been observed that each eye "sees" particular colors differently. For example, Red Group 56D can be perceived as Purple Goup 75D when viewed in slightly different light.

Similarly, a flower which has faded slightly in storage after collection can change from Purple Group 75D to Red Group 56D.

A comparison of the three editions of the RHS Colour Chart and a discussion of the issues of variations in perception of color have been made in a paper by Donald H. Voss and William N. Hale in Horticultura Science (Volume 33, Number 1, pages 13–17, published Feb. 1998) the contents of which are incorporated herein by reference.

I claim:

1. An essential oil extract comprising an extract derived from a plant of the genus Leptospermum species liversidgei, said plant being able to block the carbon dioxide message to mosquitoes and/or fleas within the vicinity of its locus.

2. An essential oil extract as claimed in claim 1, wherein said plant has a content of citronellal and/or the citronellal analogues isopulegol and pulegol which falls substantially within the range of 55–95% of total extractable oil content.

3. An essential oil extract which is from the plant identified by the RAPD fragment analysis given in FIG. 3; wherein RAPD fragments are formed using primers 2.01–2.02 and fragments of standard size are included on each gel and are indicated as $S_A$ or $S_B$.

4. An essential oil composition comprising an essential oil extract derived from a plant of the genus Leptospermum species liversidgei, said plant being able to block the carbon dioxide message to mosquitoes and/or fleas within the vicinity of its locus, and a carrier material for carrying the oil extract to the possible location of the mosquitoes and/or fleas.

5. A composition as claimed in claim 4 wherein the plant contains 55–95% citronellal and/or the citronellal analogues isopulegol and pulegol of total extractable oil content.

6. A composition as claimed in claim 5 wherein the plant has the RAPD fragment analysis given in FIG. 3; wherein RAPD fragments are formed using primers 2.01–2.02 and fragments of standard size are included on each gel and are indicated as $S_A$ or $S_B$.

7. An essential oil extract as claimed in claim 1 wherein said plant has the following parts and morphological features:

a shrub being erect, compact, 0.5–3.0 meters tall and 1–1.5 meters wide, mostly single trunked having numerous erect branches occasionally lightly weeping ends and the branches being sericeous and soon becoming glabrous;

bark being hard, tight, grey, and flaking in patches near the base;

leaves being shortly petiolate, alternative, densely arranged up the stems and seldom spreading, said leaves being flexible, apex obtuse, 3–8 mm long×1.5–3 mm wide, glabrous, having new growth of the RHS Green group 141C; mature leaves of the RHS Green group 141A, and including oil glands being small, numerous, and emitting a citrus-like scent when crushed; and flowers being solitary, sessile, mainly in axils, hypanthium 3–5 mm long×3–4 mm wide, glabrous and occasionally sparsely sericeous; sepals being ca 1.5 mm long; petals being light pink in the RHS Red group 56D, and being ca 5–7 mm long×4–5 mm wide and including numerous stamens C.15–20, ovary being of the five locular, domed, and glabrous.

8. An essential oil extract as claimed in claim 1, wherein said plant is a clone of a parent plant of the genus Leptospermum species liversidgei, the parent plant having sufficient citronellal content to block the carbon dioxide message to mosquitoes and/or fleas within the vicinity of its locus.

9. An essential oil extract as claimed in claim 2, wherein said plant has a content of citronellal and/or the citronellal analogues isopulegol and pulegol which falls substantially within the range of 70–95% of total extractable oil content.

10. A composition as claimed in claim 4 in which the plant has the following morphological features:

a shrub being erect, compact, 0.5–3.0 meters tall and 1–1.5 meters wide, mostly single trunked having numerous erect branches occasionally lightly weeping ends and the branches being sericeous and soon becoming glabrous;

bark being hard, tight, grey, and flaking in patches near the base;

leaves being shortly petiolate, alternative, densely arranged up the stems and seldom spreading, said leaves being flexible, apex obtuse, 3–8 mm long×1.5–3 mm wide, glabrous, having new growth of the RHS Green group 141C; mature leaves of the RHS Green group 141A, and including oil glands being small, numerous, and emitting a citrus-like scent when crushed; and flowers being solitary, sessile, mainly in axils, hypanthium 3–5 mm long×3–4 mm wide, glabrous and occasionally sparsely sericeous; sepals being ca 1.5 mm long; petals being light pink in the RHS Red group 56D, and being ca 5–7 mm long×4–5 mm wide and including numerous stamens C.15–20, ovary being of the five locular, domed, and glabrous.

11. An essential oil extract as claimed in claim 4, wherein said plant is a clone of a parent plant of the genus Leptospermum species liversidgei, the parent plant having sufficient citronellal content to block the carbon dioxide message to mosquitoes and/or fleas within the vicinity of its locus.

12. An essential oil extract as claimed in claim 5, wherein said plant has a content of citronellal and/or the citronellal analogues isopulegol and pulegol which falls substantially within the range of 70–95% of total extractable oil content.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 10
      (B) TYPE: Nucleic Acid
      (C) STRANDEDNESS: Double
      (D) TOPOLOGY: Linear (xi) SEQUENCE DESCRIPTION: SEQ ID NO: 1:

AAGCTGCGAG                                                          10

(2) INFORMATION FOR SEQ ID NO: 2:

(i) SEQUENCE CHARACTERISTICS:
      (A) LENGTH: 10
      (B) TYPE: Nucleic Acid
      (C) STRANDEDNESS: Double
      (D) TOPOLOGY: Linear (xi) SEQUENCE DESCRIPTION: SEQ ID NO: 2:

CACGGCGAGT                                                          10

(2) INFORMATION FOR SEQ ID NO: 3:

(i) SEQUENCE CHARACTERISTICS:
      (A) LENGTH: 10
      (B) TYPE: Nucleic Acid
      (C) STRANDEDNESS: Double
      (D) TOPOLOGY: Linear (xi) SEQUENCE DESCRIPTION: SEQ ID NO: 3:

CTGGCGTGAC                                                          10

(2) INFORMATION FOR SEQ ID NO: 4:

(i) SEQUENCE CHARACTERISTICS:
      (A) LENGTH: 10
      (B) TYPE: Nucleic Acid (C) STRANDEDNESS: Double
            (D) TOPOLOGY: Linear (xi) SEQUENCE DESCRIPTION: SEQ ID NO: 4:

GGGTAACGCC                                                              10

(2) INFORMATION FOR SEQ ID NO: 5:

(i) SEQUENCE CHARACTERISTICS:
            (A) LENGTH: 10
            (B) TYPE: Nucleic Acid
            (C) STRANDEDNESS: Double
            (D) TOPOLOGY: Linear (xi) SEQUENCE DESCRIPTION: SEQ ID NO: 5:

CAATCGCCGT                                                              10

(2) INFORMATION FOR SEQ ID NO: 6:

(i) SEQUENCE CHARACTERISTICS:
            (A) LENGTH: 10
            (B) TYPE: Nucleic Acid
            (C) STRANDEDNESS: Double
            (D) TOPOLOGY: Linear (xi) SEQUENCE DESCRIPTION: SEQ ID NO: 6:

TTCGAGCCAG                                                              10

(2) INFORMATION FOR SEQ ID NO: 7:

(i) SEQUENCE CHARACTERISTICS:
            (A) LENGTH: 10
            (B) TYPE: Nucleic Acid
            (C) STRANDEDNESS: Double
            (D) TOPOLOGY: Linear (xi) SEQUENCE DESCRIPTION: SEQ ID NO: 7:

GAACGGACTC                                                              10

(2) INFORMATION FOR SEQ ID NO: 8:

(i) SEQUENCE CHARACTERISTICS:
            (A) LENGTH: 10
            (B) TYPE: Nucleic Acid
            (C) STRANDEDNESS: Double
            (D) TOPOLOGY: Linear (xi) SEQUENCE DESCRIPTION: SEQ ID NO: 8:

GTCCCGACGA                                                              10

(2) INFORMATION FOR SEQ ID NO: 9:

(i) SEQUENCE CHARACTERISTICS:
            (A) LENGTH: 10
            (B) TYPE: Nucleic Acid
            (C) STRANDEDNESS: Double
            (D) TOPOLOGY: Linear (xi) SEQUENCE DESCRIPTION: SEQ ID NO: 9:

TGTCATCCCC                                                              10

(2) INFORMATION FOR SEQ ID NO: 10:

(i) SEQUENCE CHARACTERISTICS:
            (A) LENGTH: 10
            (B) TYPE: Nucleic Acid
            (C) STRANDEDNESS: Double

```
        (D) TOPOLOGY: Linear (xi) SEQUENCE DESCRIPTION: SEQ ID NO: 10:

GGTGATCAGG                                                              10

(2) INFORMATION FOR SEQ ID NO: 11:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 11:

CCGAATTCCC                                                              10

(2) INFORMATION FOR SEQ ID NO: 12:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 12:

GGCTGCAGAA                                                              10

(2) INFORMATION FOR SEQ ID NO: 13:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 13:

CTGACCAGCC                                                              10

(2) INFORMATION FOR SEQ ID NO: 14:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 14:

GTCCCGTGGT                                                              10

(2) INFORMATION FOR SEQ ID NO: 15:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 15:

CCACACTACC                                                              10

(2) INFORMATION FOR SEQ ID NO: 16:

(i) SEQUENCE CHARACTERISTICS:
        (A) LENGTH: 10
        (B) TYPE: Nucleic Acid
        (C) STRANDEDNESS: Double
        (D) TOPOLOGY: Linear
```

-continued (xi) SEQUENCE DESCRIPTION: SEQ ID NO: 16:

CACCCGGATG                                                                      10

(2) INFORMATION FOR SEQ ID NO: 17:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 17:

CACAGGCGGA                                                                      10

(2) INFORMATION FOR SEQ ID NO: 18:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 18:

TGACCCGCCT                                                                      10

(2) INFORMATION FOR SEQ ID NO: 19:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 19:

GGACGGCGTT                                                                      10

(2) INFORMATION FOR SEQ ID NO: 20:

(i) SEQUENCE CHARACTERISTICS:
        (A) LENGTH: 10
        (B) TYPE: Nucleic Acid
        (C) STRANDEDNESS: Double
        (D) TOPOLOGY: Linear (xi) SEQUENCE DESCRIPTION: SEQ ID NO: 20:

TGGCGCAGTG                                                                      10